United States Patent
Keith et al.

(10) Patent No.: US 7,115,103 B2
(45) Date of Patent: Oct. 3, 2006

(54) STROKE SYMPTOM RECOGNITION DEVICES AND METHODS

(76) Inventors: Peter Trexler Keith, 1477 Grantham St., St. Paul, MN (US) 55108; Robert Emmett Atkinson, 2679 Riviera Dr. South, White Bear Lake, MN (US) 55110

( * ) Notice: Subject to any disclaimer, the term of this patent is extended or adjusted under 35 U.S.C. 154(b) by 321 days.

(21) Appl. No.: 10/641,833

(22) Filed: Aug. 15, 2003

(65) Prior Publication Data

US 2004/0044273 A1     Mar. 4, 2004

Related U.S. Application Data

(60) Provisional application No. 60/460,525, filed on Apr. 4, 2003, provisional application No. 60/429,101, filed on Nov. 26, 2002, provisional application No. 60/407,370, filed on Aug. 31, 2002.

(51) Int. Cl.
*A61B 5/103* (2006.01)
*A61B 5/117* (2006.01)

(52) U.S. Cl. ........................... 600/587; 600/595

(58) Field of Classification Search ........ 600/587, 600/595
See application file for complete search history.

(56) References Cited

U.S. PATENT DOCUMENTS

| | | | |
|---|---|---|---|
| 4,307,608 A * | 12/1981 | Useldinger et al. | ...... 73/379.01 |
| 4,592,371 A | 6/1986 | Pellicano et al. | |
| 4,882,677 A | 11/1989 | Curran | |
| 4,884,445 A | 12/1989 | Sadoff et al. | |
| 4,949,729 A | 8/1990 | Haski | |
| 5,090,421 A | 2/1992 | Wagoner, III | |
| 5,125,270 A | 6/1992 | Kovacebic | |
| 5,157,970 A | 10/1992 | Lewis, Jr. | |
| 5,159,935 A | 11/1992 | Sackner et al. | |
| 5,163,443 A * | 11/1992 | Fry-Welch et al. | ......... 600/595 |
| 5,329,813 A | 7/1994 | Lewis, Jr. | |
| 5,401,224 A | 3/1995 | Tsuchiya et al. | |
| 5,551,445 A | 9/1996 | Nashner | |
| 5,555,894 A * | 9/1996 | Doyama et al. | ............ 600/595 |
| RE35,598 E | 9/1997 | Sadoff et al. | |
| 5,678,317 A | 10/1997 | Stefanakos | |
| 5,772,605 A | 6/1998 | Weijand | |
| 5,778,885 A * | 7/1998 | Doyama et al. | ............ 600/595 |
| 5,885,231 A | 3/1999 | Cramer et al. | |
| 5,912,658 A | 6/1999 | Bergamasko et al. | |
| 5,913,835 A | 6/1999 | Naoi et al. | |
| 6,045,517 A | 4/2000 | Williams | |
| 6,047,203 A | 4/2000 | Sackner et al. | |
| 6,235,489 B1 | 5/2001 | Jackowski | |
| 6,413,098 B1 | 7/2002 | Tallal et al. | |

\* cited by examiner

*Primary Examiner*—Max F. Hindenburg
*Assistant Examiner*—Anuradha Roy

(57) ABSTRACT

Devices and methods for detecting one or more symptoms of stroke, such as motor function deficits and cognitive function deficits. By way of example, not limitation, the present invention provides devices and methods for detecting various forms of hemiparesis, ataxia, aphasia, and/or dysarthria, which may be measured alone or in any combination.

19 Claims, 15 Drawing Sheets

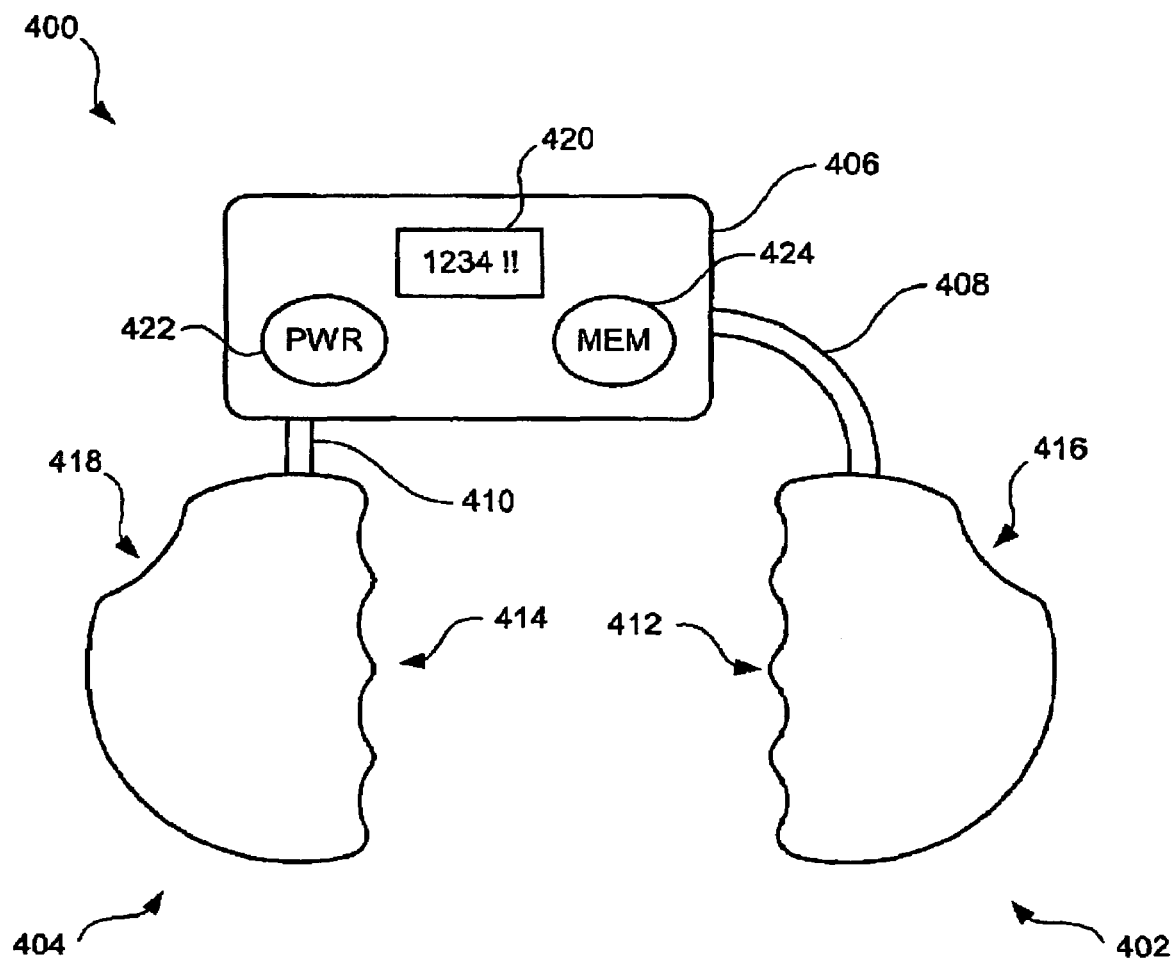
FIG. 10
(AMENDED)

STROKE SYMPTOM RECOGNITION DEVICES AND METHODS

CROSS-REFERENCE TO RELATED CASES

The present application claims the benefit of U.S. Provisional Patent Application No. 60/407,370 filed Aug. 31, 2002, entitled STROKE DETECTION DEVICE AND METHOD, U.S. Provisional Patent Application No. 60/429,101 filed Nov. 26, 2002, entitled STROKE DETECTION DEVICE AND METHOD, and U.S. Provisional Patent Application No. 60/460,525 filed Apr. 4, 2003, entitled STROKE SYMPTOM RECOGNITION DEVICE AND METHOD.

FIELD OF THE INVENTION

The present invention generally relates to medical diagnostic devices and methods. More specifically, the present invention relates to medical devices and methods for diagnosing symptoms of stroke.

BACKGROUND OF THE INVENTION

Stroke is a leading cause of death and disability in industrialized nations. Nearly 500,000 people in the United States suffer from stroke syndromes annually, at a cost of $23 billion. Strokes are caused primarily by an abrupt interruption of blood flow to a portion of the brain, due to arterial blockage. A less common cause of stroke is hemorrhaging due to a ruptured cerebral aneurysm.

Since strokes affect only one side of the brain, symptoms typically involve only one side of the body. Common symptoms include muscle weakness, numbness, paralysis, vision problems, loss of balance, loss of coordination, and speech impairment. These symptoms are often subjective, and often not easily discernable by the user. Furthermore, symptoms of stroke are rarely painful, unlike those in a heart attack. Therefore, people suffering from stroke are often not aggressive and inherently reluctant in seeking medical attention.

However, prompt medical attention is crucial for implementing treatment modalities that can dramatically minimize the long-term impact of the stroke for the user. One such therapy is the use of thrombolytic agents ("clot busters") to restore blood flow to the ischemic zone. But, the effectiveness of this treatment drops off rapidly after the first hours following stroke. Moreover, after 3 hours of symptom onset, use of thrombolytics dramatically increases the risk of hemorrhaging, substantially worsening the outlook for the user.

Studies have indicated that only about 25% of stroke users arrive to a hospital in less than 2 hours, while approximately 60% arrive after 6 hours, well beyond the time window for effective treatment. The primary cause of this delay is the delay in the user deciding to seek medical attention. Clearly, public health care would be greatly benefited if more stroke users could present to a hospital in a more timely fashion.

There is therefore a great need for a user-implemented diagnostic tool to quickly, easily, and objectively diagnose symptoms related to the onset of stroke. Such a tool would help a user suffering a stroke to seek prompt medical attention.

SUMMARY OF THE INVENTION

The present invention provides exemplary embodiments of devices and methods for detecting one or more symptoms of stroke, such as motor function deficits and cognitive function deficits. By way of example, not limitation, the present invention provides devices and methods for detecting various forms of hemiparesis, ataxia, aphasia, and/or dysarthria, which may be measured alone or in any combination. Generally speaking, the devices and methods of the present invention provide for the measurement of various indicia of the above symptoms, and provide for various actions (e.g., alert signal, EMS notification, etc.) if the measurement(s) meet certain predefined conditions (e.g., above or below a threshold value).

In some embodiments of the present invention, devices and methods are provided for detecting hemiparesis. Hemiparesis, a very common symptom of stroke, is a muscular weakness or partial paralysis restricted to one side of the body. Exemplary embodiments are disclosed for detecting hemiparesis by measuring differences in hand strength or arm drift.

In other embodiments of the present invention, devices and methods are provided for detecting ataxia. Ataxia is an impaired ability to perform smooth coordinated voluntary movements. Exemplary embodiments are disclosed for detecting ataxia by measuring dexterity.

In still other embodiments of the present invention, devices and methods are provided for detecting aphasia, including receptive aphasia and expressive aphasia. Aphasia is a cognitive disorder marked by an impaired ability to comprehend (receptive aphasia) or express (expressive aphasia) language. Exemplary embodiments are disclosed for detecting receptive aphasia by positing written or oral instructions to the user, followed by measuring the correctness and/or time delay of the response from the user. Exemplary embodiments are also disclosed for detecting expressive aphasia by positing an image of an object to the user, prompting the user to identify or name the object, and measuring the correctness and/or time delay of the response from the user.

In yet other embodiments of the present invention, devices and methods are provided for detecting dysarthria. Dysarthria is a disorder of speech articulation (e.g., slurred speech). Exemplary embodiments are disclosed for detecting dysarthria by prompting the user to say a word or phrase that is recorded for subsequent comparison by voice pattern recognition techniques or evaluation by medical personnel.

The devices and methods of the present invention may be implemented in devices dedicated to detecting one or more stroke symptoms. Alternatively, the devices and methods of the present invention may be incorporated into a device wherein the diction of stroke symptoms is an ancillary function. For example, the devices and methods of the present invention may be incorporated into a personal digital assistant (PDA), a cellular phone, or other portable electronic device. In addition, the methods described herein may be completely or partially implemented in hardware or software (e.g., executable code) of such portable electronic devices.

Thus, with the devices and methods of the present invention, a stroke victim is better able to ascertain symptoms associated with the onset of stroke, and more quickly seek medical attention, thereby reducing the time for implementation of time sensitive therapies (e.g., thrombolytic therapy) and improving the patient's long term outcome.

BRIEF DESCRIPTION OF THE DRAWINGS

FIG. 10 is a plan view of a pneumatic bilateral hand strength measurement device;

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Hemiparesis Detection Devices & Methods

Figure 1A:
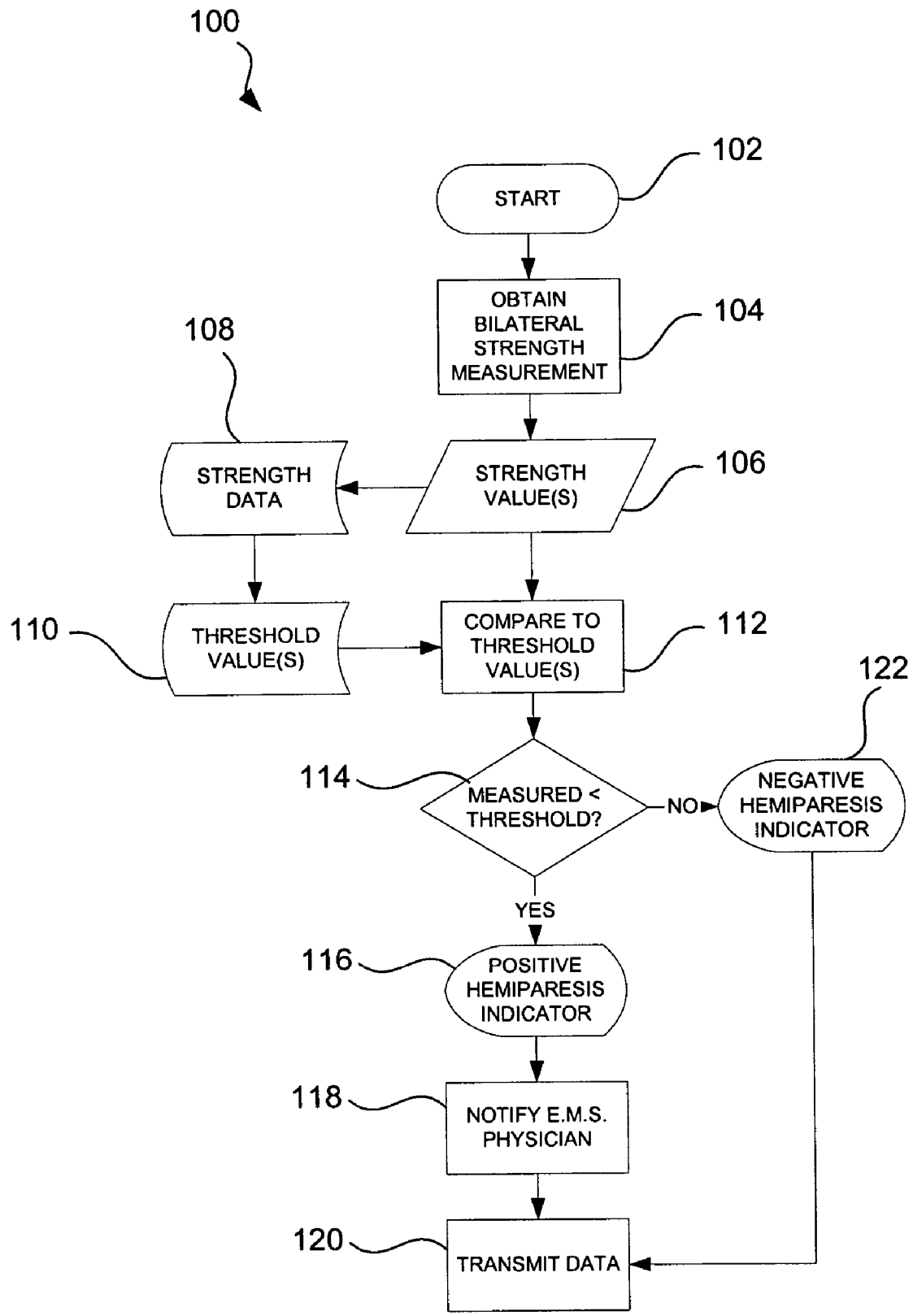
FIG. 1A is a flow chart illustrating a method of detecting hemiparesis using a bilateral strength measurement device.
Figure 3:
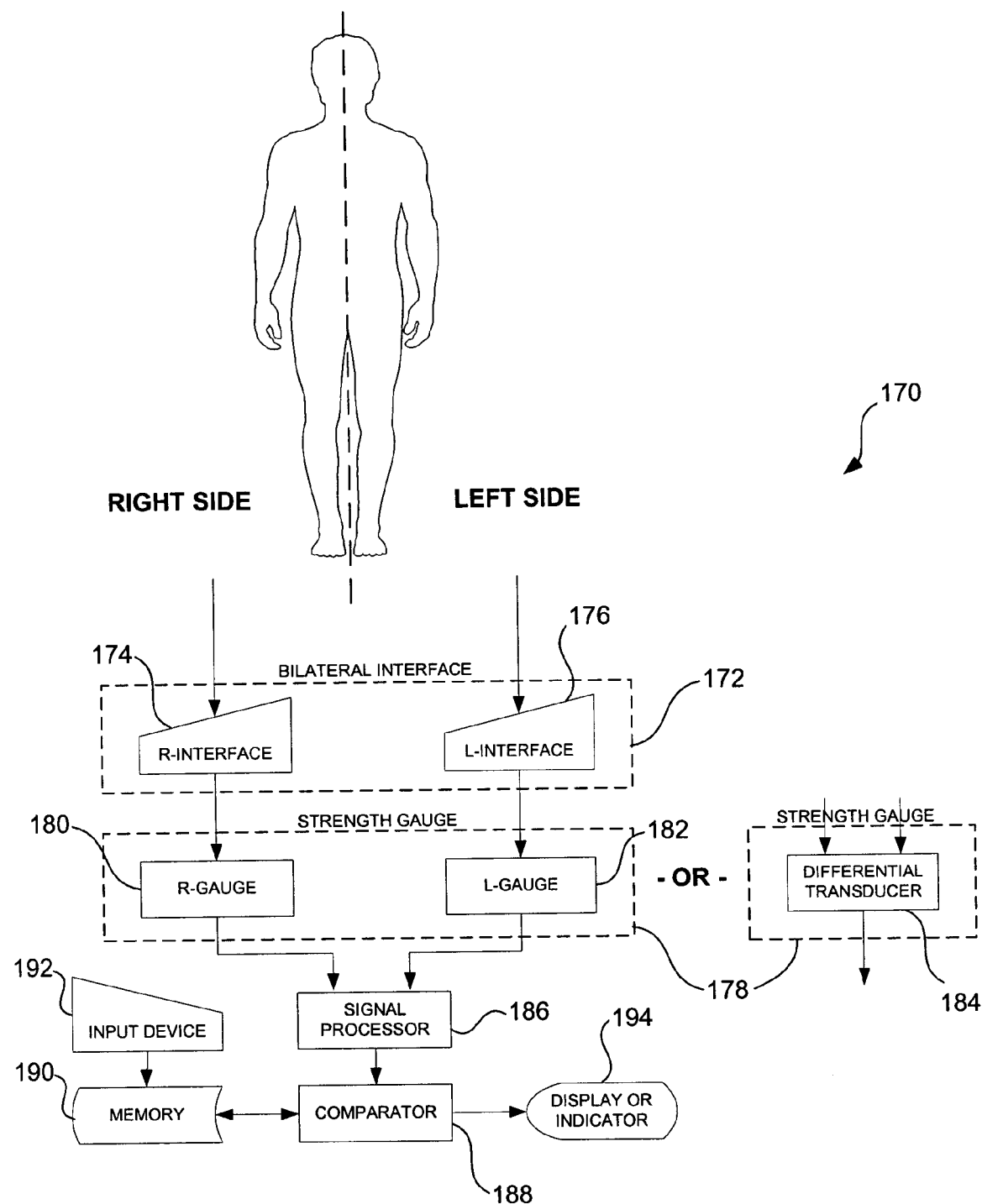
FIG. 3 is a schematic functional illustration of a bilateral strength measurement device incorporating electronic circuitry.

With reference to FIG. 1A, a method 100 of detecting hemiparesis using a bilateral strength measurement device is shown. In this illustrative method, a bilateral device (not shown) may be utilized to measure strength, such the bilateral device is schematically illustrated in FIG. 3. For purposes of the following description of method 100, the bilateral device generally includes a right side body interface, a left side body interface, and a strength gauge.

The method starts with step 102, which may correspond to powering on the bilateral device. The interfaces of the bilateral device are connected to the respective right and left sides of the user, and the user applies force independently to each of the interfaces, preferably at (approximately) the same time. To ensure that forces are applied at approximately the same time, a timer (clock) with a pre-set time interval may be used to define a sampling window in which the forces must be applied to generate strength values 106.

With the interfaces connected to the right and left sides of the user, and upon the application of force (e.g., compression, torsion, etc.), one or more strength measurements are taken 104 to generate strength values 106. The measured strength values 106 may comprise one or more discrete measurements of the right and left sides, or one or more differential measurements between the right and left sides. The one or more strength measurements may be taken during a given sample period, and multiple measurements may be averaged over the sampling period.

The measured strength values 106 may be stored as strength data 108 in a suitable memory storage device. The strength data 108 may be used to generate or derive threshold values 110, which may also be stored in the memory storage device. For purposes of storing the threshold values, the memory storage device may comprise a mechanical indicator or stop mechanism, an electronic circuit, or a computer-based memory storage device, for example. The threshold values 110 may be specific to the user, or based on population data. The threshold values 110 may correspond to strength measurements (discrete or differential) of the user or population in a non-hemiparetic (i.e., healthy) condition, and thus may serve as a basis for comparison 112 to the measured strength values 106.

The basis for comparison 112 may be a function of the type of measured strength values 106 and the type of threshold values 110. For example, if discrete lateral (one-side) measurements are taken, the measured right strength value may be compared to a threshold right strength value, and the measured left strength value may be compared to a threshold left strength value. Alternatively, if a differential measurement is taken, the measured strength differential may be compared to threshold strength differential. The comparison may be performed manually (i.e., by the user), or automatically, such as by electronic circuitry or an algorithm stored in memory and executed by a microprocessor.

As shown in step 114, if the comparison 112 shows that the measured strength value(s) is (are) greater than or equal to the threshold value(s) 110, a negative hemiparesis indicator 122 may be triggered. If the comparison shows that the measured strength value(s) is (are) less than the threshold value(s), a positive hemiparesis indicator 116 may be triggered, which may be indicative of hemiparesis and stroke. This indicator 116 urges the user to seek medical attention as soon as possible to maximize the opportunity to quickly diagnose and treat a stroke event.

In the alternative, such as when no reliable basis for comparison is available, the measured values may simply be compared to each other (i.e., right compared to left or left compared to right). A significant difference between the right and left strength measurements may be indicative of hemiparesis and stroke.

Although a direct comparison is described herein for purposes of illustration, it is also possible to mathematically alter the measured strength values, the threshold values and/or the algorithm defining the comparison to meet the same or similar objective of detecting a decrease in strength, particularly isolated to one side of the body, which may be indicative of hemiparesis and stroke.

If a positive hemiparesis indicator 116 is triggered, a physician and/or an emergency medical service (EMS), such as a public medical emergency service (911), a private medical emergency service, or a hospital emergency room, may be automatically notified 118 of the hemiparetic event utilizing a telecommunications link, for example. The EMS and/or physician then have the opportunity to contact the user and/or provide medical attention to the user as soon as possible to maximize the opportunity to quickly diagnose and treat a stroke event. Whether a positive hemiparesis indicator 116 or a negative hemiparesis indicator 122 is triggered, the measured strength values 106 may be transmitted 120 to a medical database (e.g., physician's network), which allows the physician to track the user's status and, for example, contact the user if the data suggests a gradual change in condition.

Figure 1B:
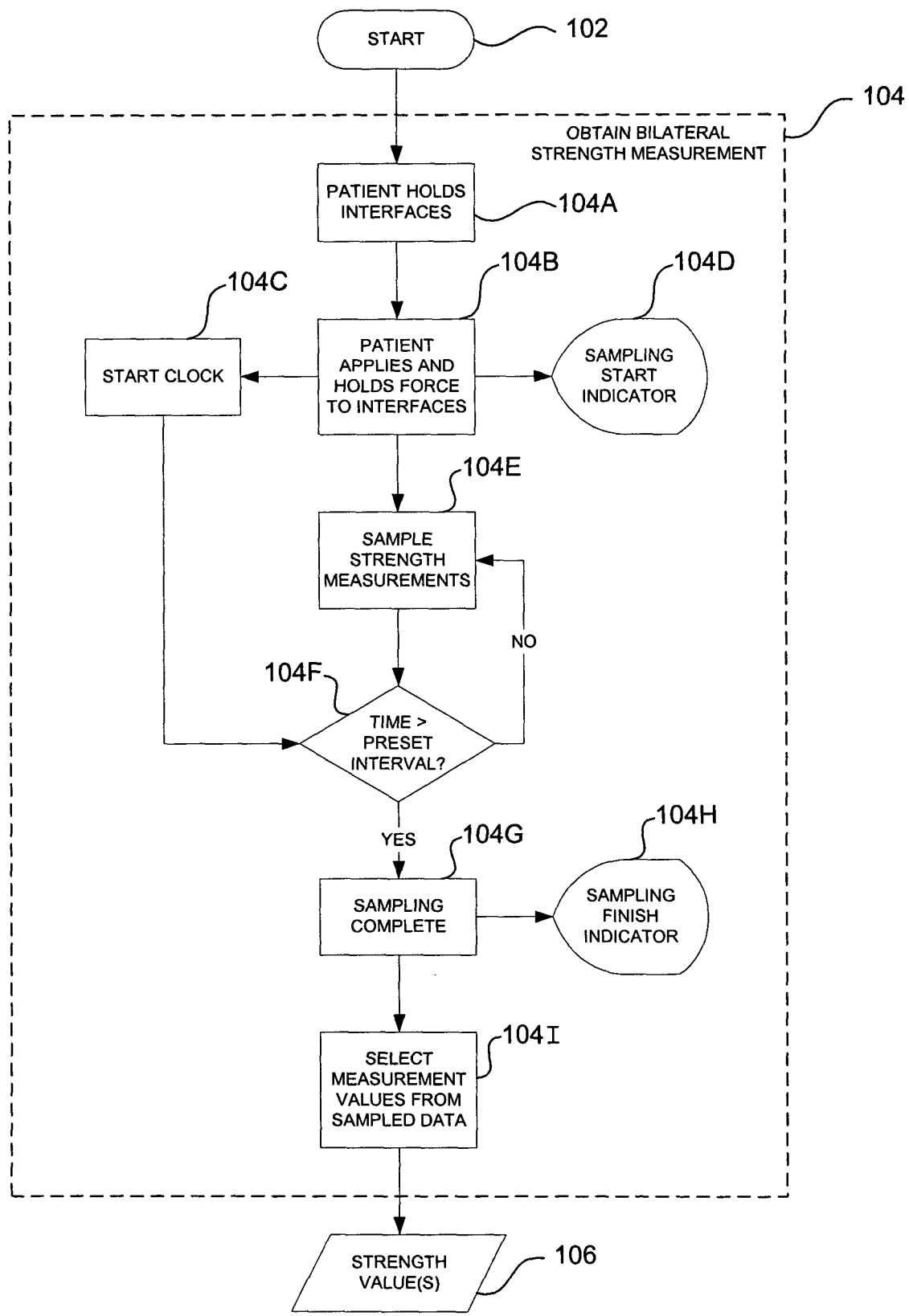
FIG. 1B is a flow chart detailing a step of the method illustrated in FIG. 1A.

With reference to FIG. 1B, the step 104 of obtaining bilateral strength measurement(s) is detailed. Obtaining 104 the strength measurements begins with the user holding 104A or otherwise engaging the interfaces of the bilateral device. The user then applies and holds a force (e.g., compression, torque, etc.) 104B to the interfaces, which starts a timer clock 104C and triggers a sampling start indicator 104D (e.g., audible, visible) which notifies the user to continue to apply (maximum) force to the interfaces. Strength measurements are then sampled 104E periodically (e.g., every 0.01 seconds) during the sampling period until the expiration of time as dictated by timer loop 104F. Once the time has expired, the sampling is complete 104G and a sampling finish indicator is triggered 104G which notifies the user that he/she may stop applying force to the interfaces. From the sampled strength data, certain strength measurement values are selected 104I, such as the maximum value, average value(s), or values obtained during the sampling period.

Figure 2:
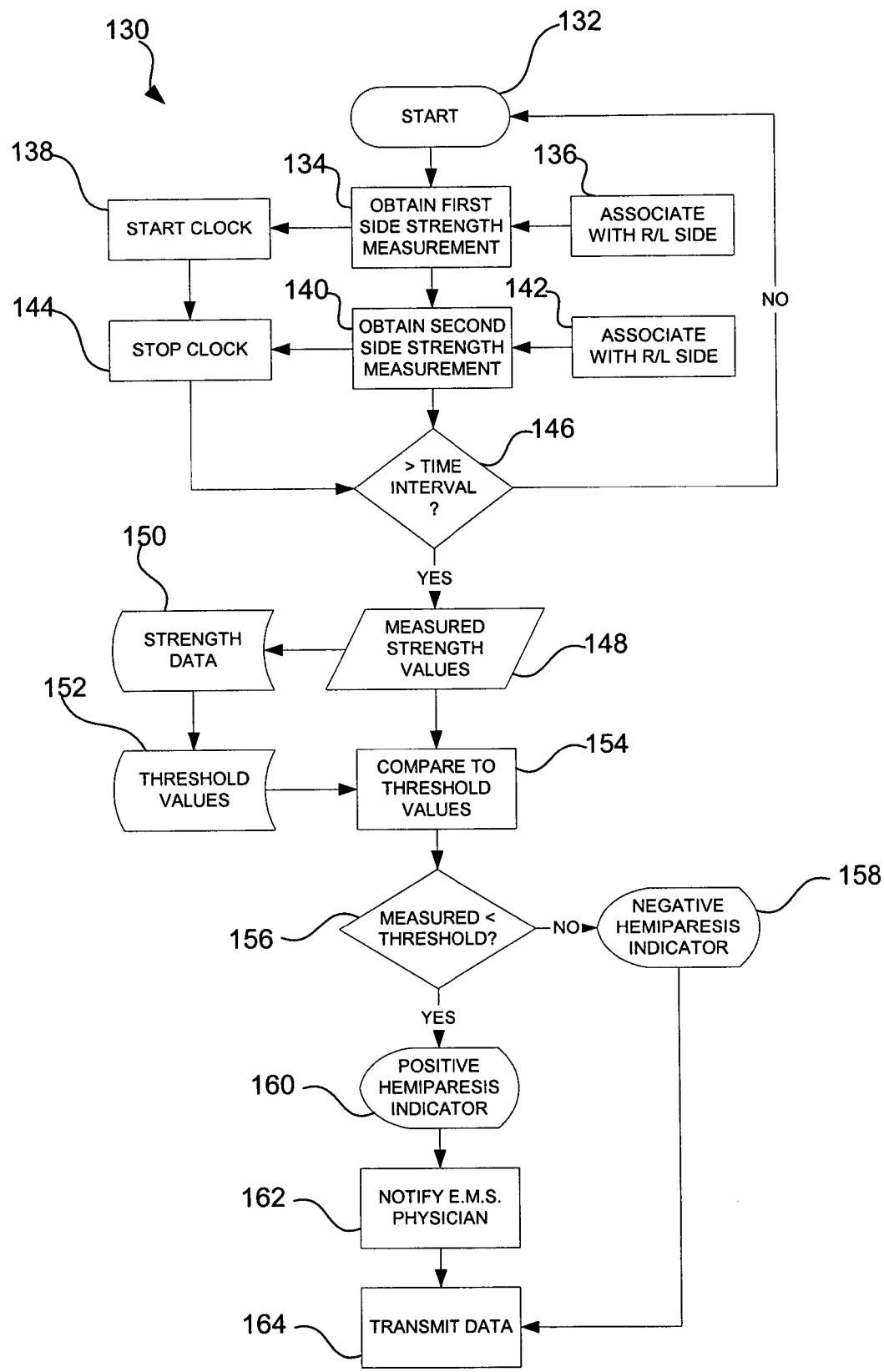
FIG. 2 is a flow chart illustrating a method of detecting hemiparesis using a unilateral (or bilateral) strength measurement device.

With reference to FIG. 2, a method 130 of detecting hemiparesis using a unilateral (or bilateral) strength measurement device is shown. In this illustrative method, a unilateral or bilateral device (not shown) may be utilized to measure strength, such the unilateral device schematically illustrated in FIG. 4 or the bilateral device schematically illustrated in FIG. 3. The method 130 described with reference to FIG. 2 is particularly suited for and is described with reference to a unilateral device, which generally includes a single lateral side interface and a strength gauge. Note that some of the bilateral devices described herein may be used as a unilateral device by using only one side of the interfaces.

The illustrated method 130 starts with step 132, which may correspond to powering on the unilateral device. The interface of the unilateral device is connected to either the right or left side of the user, and the user applies force to the interface to obtain a first side strength measurement 134. The first side strength measurement 134 is ten associated 136 with either the right or left side, which may be accomplished manually (e.g., manual input) or automatically (e.g., a predefined process which dictates that the user start with a particular side). Upon the application of force to the interface, a clock (timer) may be started 138 to ensure that forces are applied within a desired time interval. The interface of the unilateral device is then connected to the opposite side of the user, and the user applies force to the interface to obtain a second side strength measurement 140. The second side strength measurement 140 is then associated 142 with either the right or left side, which may be accomplished manually (e.g., manual input) or automatically (e.g., a predefined process which assumes the opposite association as the first measurement 134). When the second side measurement is taken, the clock (timer) is stopped 144, and the elapsed time is compared 146 to the preset time interval to see if the measurements were taken within the desired sampling window. If the measurements were not taken sufficiently close in time as defined by the preset time interval, the process begins again and new strength measurements may be obtained. If the measurements were taken within the desired sampling period, the strength measurements become strength values 146.

The measured strength values 146 may comprise discrete measurements of the right and left sides, and may be stored as strength data 150 in a suitable memory storage device. The strength data 150 may be used to generate or derive threshold values 152, which may also be stored in the memory storage device. For purposes of storing the threshold values, the memory storage device may comprise a mechanical indicator or stop mechanism, an electronic circuit, or a computer-based memory storage device, for example. The threshold values 152 may be specific to the user, or based on population data. The threshold values 152 may correspond to strength measurements of the user or population in a non-hemiparetic (i.e., healthy) condition, and thus may serve as a basis for comparison 154 to the measured strength values 148. For example, the measured right strength value may be compared to a threshold right strength value, and the measured left strength value may be compared to a threshold left strength value. Alternatively, difference between the right and left measured strength values may be compared to a threshold value corresponding to difference between the right and left strength. The comparison may be performed manually (i.e., by the user), or automatically, such as by electronic circuitry or an algorithm stored in memory and executed by a microprocessor.

As shown in step 156, if the comparison 154 shows that the measured strength values are greater than or equal to the threshold values 152, a negative hemiparesis indicator 158 may be triggered. If the comparison shows that the measured strength values are less than the threshold values, a positive hemiparesis indicator 160 may be triggered, which may be indicative of hemiparesis and stroke. In the alternative, such as when no reliable basis for comparison is available, the measured values may simply be compared to each other (i.e., right compared to left or left compared to right). A significant difference between the right and left strength measurements may be indicative of hemiparesis and stroke. Although a direct comparison is described herein for purposes of illustration, it is also possible to mathematically alter the measured strength values, the threshold values and/or the algorithm defining the comparison to meet the same or similar objective of detecting a decrease in strength, particularly isolated to one side of the body, which may be indicative of hemiparesis and stroke.

If a positive hemiparesis indicator 160 is triggered, a physician and/or an emergency medical service (EMS) may be automatically notified 162 of the hemiparetic event utilizing a telecommunications link, for example. Whether a positive hemiparesis indicator 160 or a negative hemiparesis indicator 158 is triggered, the measured strength values 148 may be transmitted 164 to a medical database (e.g., physician's network).

With reference to FIG. 3, a schematic diagram of a bilateral device 170 is shown for measuring the strength of one or both of the right and left sides of a user, either simultaneously or sequentially. Further detailed exemplary embodiments of bilateral devices are described with reference to FIGS. 6–11. The bilateral device 170 generally includes a bilateral interface 172 connected to a strength gauge 178. The bilateral interface 172 includes a right side force input interface 174 and a left side force input interface 176 which connect to the right and left sides, respectively, of the user and operate independently such that the user may actuate the right side interface independently of the left side interface. The interfaces 174/176 may be configured to interface with the user's fingers, hands, arms or legs, for example. Any of the bilateral devices described herein may be implemented as a unilateral device by using only one of the interfaces 174/176.

The strength gauge 178 may comprise two individual strength gauges 180/182 or a single differential gauge 184, for example. The individual and differential strength gauges 180/182/184 may comprise transducers, pressure gauges, or force gauges (e.g., strain gauge, spring gauge, etc.), for example. Depending on the type of gauge utilized, for example if a transducer or other electronic gauge is utilized, the strength gauge 178 may be connected to a signal processor 186 which processes (e.g., amplifies, filters, etc.) the output signal(s) from the strength gauge 178.

A comparator 188 is connected to the signal processor 186, or directly to the strength gauge 178 if a signal processor 186 is not utilized. The comparator 188 is connected to a memory storage device 190 which may contain measured strength data and threshold value data. The memory storage device 190 may be coupled to an input device 192 for manually inputting threshold values. The comparator 188 performs the comparison function as described with reference to FIGS. 1 and 2, and is connected to a display or indicator 194 which may be used to display or indicate measured strength data, threshold value data, positive hemiparesis, and/or negative hemiparesis. The signal processor 186, the comparator 188, and the memory storage device 190 may be manifested as conventional electronic signal processing circuitry, or as a microprocessor device as will be described in more detail with reference to FIG. 5.

Figure 4:
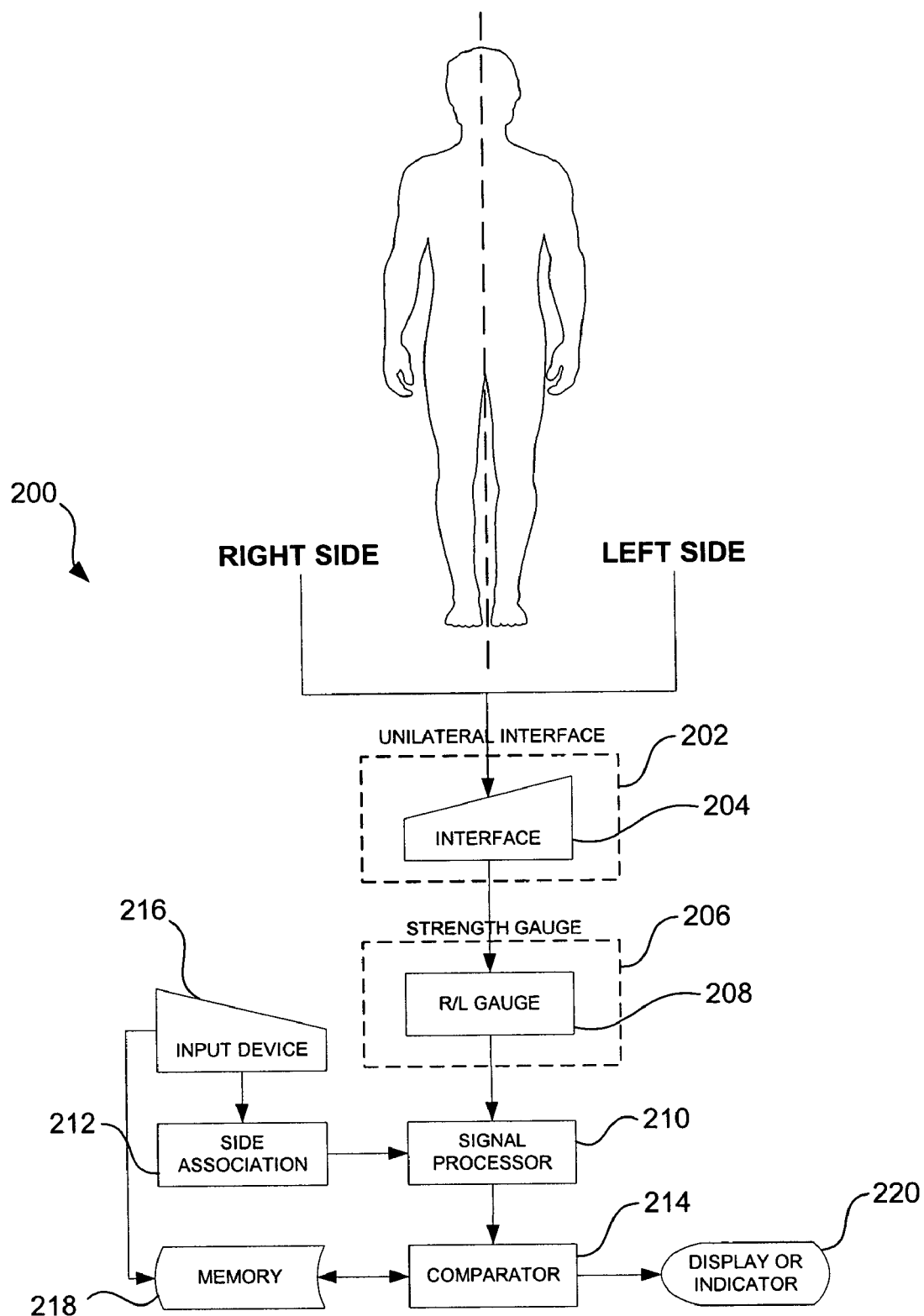
FIG. 4 is a schematic functional illustration of a unilateral strength measurement device incorporating electronic circuitry.

With reference to FIG. 4, a schematic diagram of a unilateral device 200 is shown for measuring the strength of the right and/or left sides of a user, individually or sequentially. Any of the exemplary embodiments of bilateral devices described with reference to FIGS. 6–11 may function as a unilateral device by incorporating and/or utilizing only one of the interfaces. The unilateral device 200 generally includes a unilateral interface 202 connected to a strength gauge 206. The unilateral interface 202 includes a single side force input interface 204 which is configured to individually connect to the right and left sides of the user. The interface 204 may be configured to interface with the user's fingers, hands, arms or legs, for example.

The strength gauge 206 may comprise an individual strength gauge 208 such as a transducer, pressure gauge, or force gauge (e.g., strain gauge, spring gauge, etc.), for example. Depending on the type of gauge utilized, for example if a transducer or other electronic gauge is utilized, the strength gauge 206 may be connected to a signal processor 210 which processes (e.g., amplifies, filters, etc.) the output signal from the strength gauge 206.

A side association device 212 is connected to the signal processor 210 for associating the measured strength value with the particular side (right or left) measured. The side association device may manually associate the right or left side with the measured value by utilizing an input device 216. Alternatively, the side association device may automatically associate the right or left side with the measured value by the order in which the measurements are taken (e.g., right first then left; or left first then right), wherein the user is instructed or prompted that the measurements are to be performed in a predefined order (e.g. by an instruction manual or by display 220).

A comparator 214 is connected to the signal processor 210, or directly to the strength gauge 206 if a signal processor 210 is not utilized. The comparator 214 is connected to a memory storage device 218 which may contain measured strength data and threshold value data. The memory storage device 218 may be coupled to an input device 216 for manually inputting threshold values, in addition to side association. The comparator 214 performs the comparison function as described with reference to FIG. 2, and is connected to a display or indicator 220 which may be used to display or indicate measured strength data, threshold value data, positive hemiparesis, and/or negative hemiparesis. The signal processor 210, the side association device 212, the comparator 214, and the memory storage device 218 may be manifested as conventional electronic signal processing circuitry, or as a microprocessor device as will be described in more detail with reference to FIG. 5.

Figure 5:
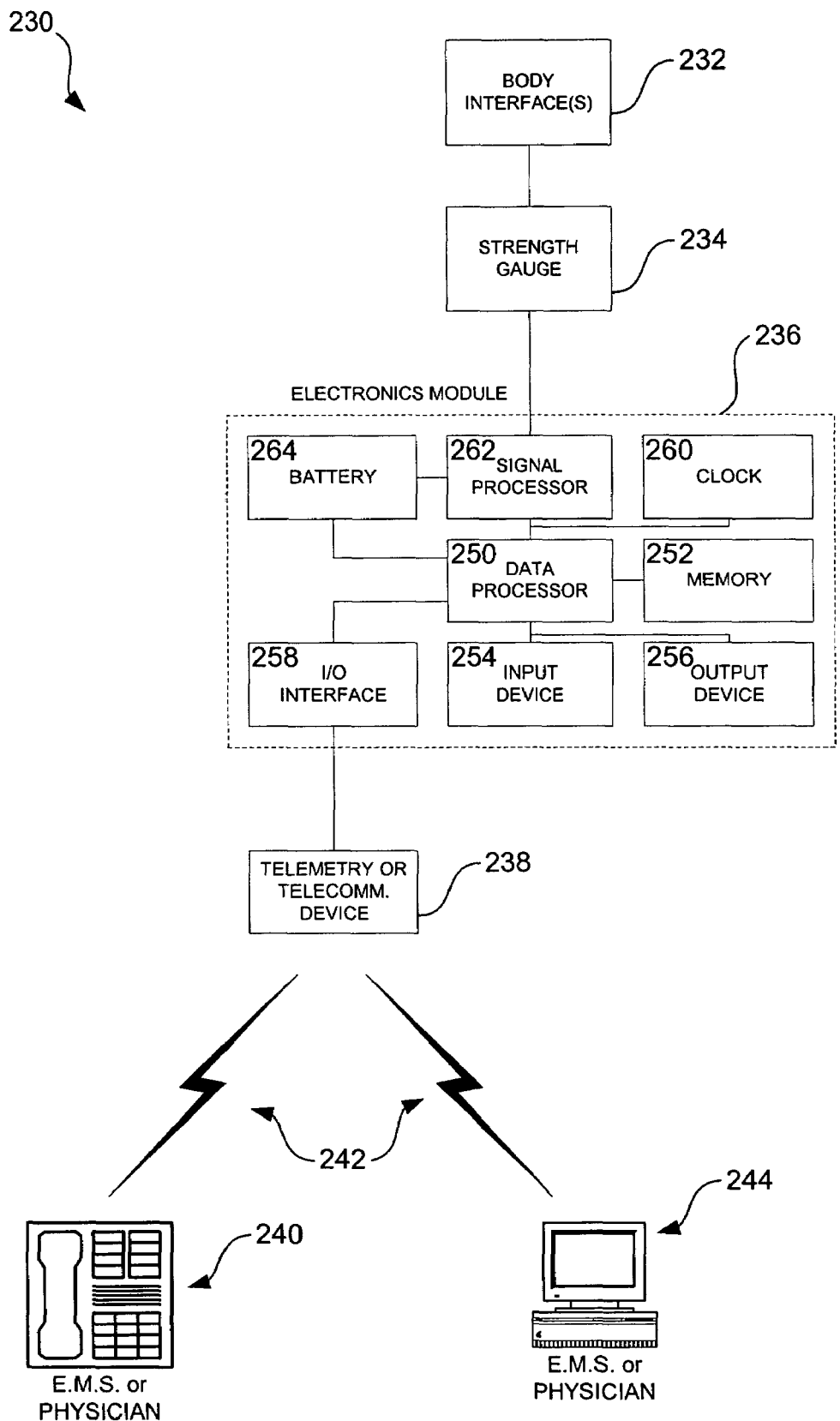
FIG. 5 is a schematic block diagram of a (bilateral or unilateral) strength measurement device incorporating an electronics module with a processor and a memory.

With reference to FIG. 5, a schematic block diagram of a bilateral or unilateral device 230 is shown including an electronics module 236. The device 230 may comprise the bilateral device shown in FIG. 3, the unilateral device shown in FIG. 4, or any of the other devices illustrated in FIGS. 6–11. The electronics module 236 is connected to a strength gauge 234 (which may comprise the strength gauge 178 shown in FIG. 3 or the strength gauge 206 shown in FIG. 4) connected to a body interface 232 (which may comprise bilateral interface 172 shown in FIG. 3 or unilateral interface 202 shown in FIG. 4).

The electronics module 236 includes a data processor 250 which may execute an algorithm to perform, among other tasks, the comparison process discussed previously. The data processor 250 is connected to memory storage device 252, which may contain the algorithm, store threshold data, store measured strength data, etc. as described previously. An input device 254 (e.g., buttons, key pad, key board) is connected to the data processor 250 to input data, commands, etc. and otherwise interact with the processor 250, memory 252 and associated algorithm. An output device 258 (e.g., LCD display, LED indicators, audio transducer, etc.) is connected to the data processor 250 to display, indicate or otherwise communicate strength data, threshold data, positive hemiparesis, negative hemiparesis, and/or any other information pertinent to the device 230 or use thereof.

The electronics module 236 may incorporate, if necessary a signal processor 262 to interface with the strength gauge 234 and process (amplify, filter, A/D conversion, etc.) signals generated by the strength gauge 234. A battery 264 or other portable power source is connected to the signal processor 262 and data processor 250 to provide the necessary electrical power to run the electronics module 236, and provide power to the strength gauge 234 if necessary. A clock circuit 260 may be connected to the data processor 250 to execute the timer functions discussed previously, or the algorithm contained in memory 252 and executed by data processor 250 may include a clock subroutine to perform the same timer functions.

An I/O interface 258 is connected to the data processor 250 to interface with external devices such as a telemetry or telecommunications device 238 (e.g., wireless transceiver, modem, cell phone, land phone, etc.). The communication device 238 is able to call, transmit data, and/or receive data to/from an EMS or physician telephone 240 or computer network 244 via telecommunication link 242 to perform, for example, the functions described with reference to FIGS. 1 and 2.

Figure 6:
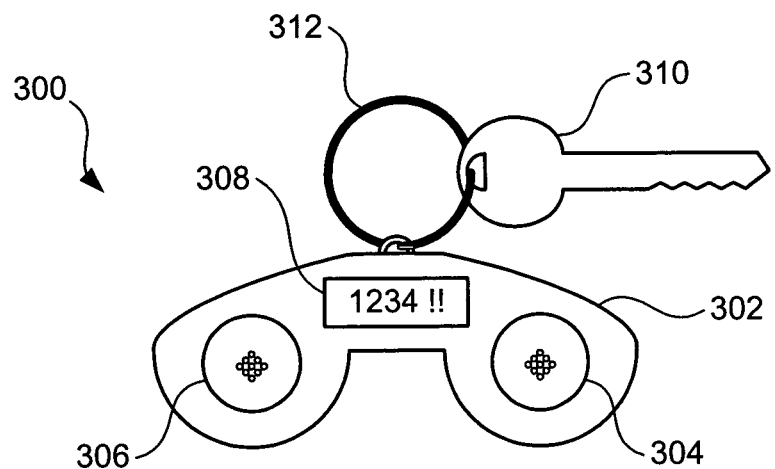
FIG. 6 is a plan view of a bilateral finger strength measurement device.

With reference to FIG. 6, a plan view of a bilateral finger strength measurement device 300 is shown. Bilateral finger device 300 is sized to be readily portable and carried in the user's clothing, pockets, or purse, much like a keyless remote for an automobile. For purposes of illustration, the size of the device 300 may be appreciated with reference to a conventional automobile key 310. To promote use and ease of access, the device 300 may be connected to the user's key ring 312 together with other important keys 310.

Bilateral finger device 300 includes a housing 302 which contains the strength gauge and electronics (not shown) discussed with reference to FIGS. 3–5. Housing 302 also contains a display 308 which may function as any of the displays, indicators, or output devices described previously. In this exemplary embodiment, the display shows a strength value ("1234") together with an alert signal ("!!"). The strength gauge (not visible) contained in housing 302 may comprise, for example, two discrete gauges as discussed with reference to FIG. 7 or a differential gauge as discussed with reference to FIG. 8.

Housing 302 further contains a pair of buttons 304/306 movably disposed therein which protrude from the top surface of the housing. The buttons 304/306 and the bottom surface (not visible) of the housing collectively define the right and left interfaces, which are configured to provide independent force inputs (as opposed to force inputs acting in opposition of each other). The buttons 304/306 and the bottom surface of the housing are configured to be grasped or pinched between the user's right and left thumbs and the user's right and left (index) fingers, respectively. The buttons 304/306 and the bottom surface of the housing may include surface irregularities (e.g., texture, protrusions, etc.) to give the user tactile feedback indicating when the interfaces are properly engaged.

Figure 7:
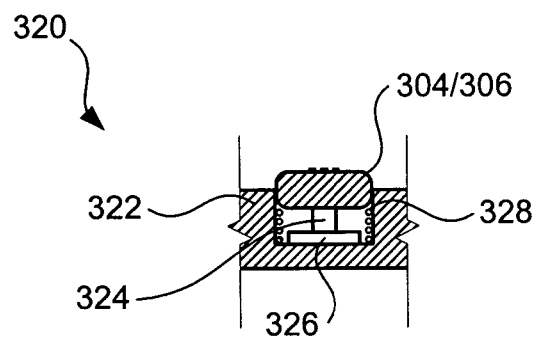
FIG. 7 is a cross-sectional view of a single body interface and a single transducer.

With reference to FIG. 7, a single button and transducer assembly 320 is shown in cross-section, two of which may be used in device 300. The assembly 320 includes a button 304/306 disposed in bore defined by a portion 322 of the housing 302. A transducer 326 (e.g., piezoelectric or piezoresistive transducer) is disposed in the bottom of the bore defined by housing portion 322, and is coupled to the button 304/306 by a compressible connector 324. A biasing member 328 (e.g., helical spring, leaf spring, etc.) may be disposed in the bore to resist movement of the button 304/306 with respect to the transducer 326 and urge the button 304/306 to protrude from the top surface of the housing 302.

Figure 8:
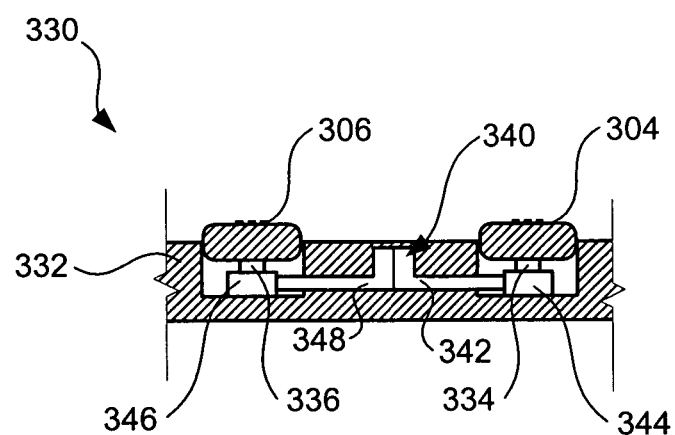
FIG. 8 is a cross-sectional view of two body interfaces and a differential transducer.

With reference to FIG. 8, a dual button and differential transducer assembly 330 for use in device 300 is shown in cross-section. The assembly 330 includes a pair of buttons 304/306 disposed in right and left bores, respectively, defined by a portion 332 of the housing 302. A differential transducer 340 is disposed in the housing portion 332 between the buttons 304/306. In this illustrative embodiment, the differential transducer 340 comprises a differential pressure transducer. The differential pressure transducer 340 is in fluid communication with a piston 334 and barrel 344 assembly associated with right button 304 via conduit 342, and a piston 336 and barrel 346 assembly associated with left button 306 via conduit 348.

Figure 9:
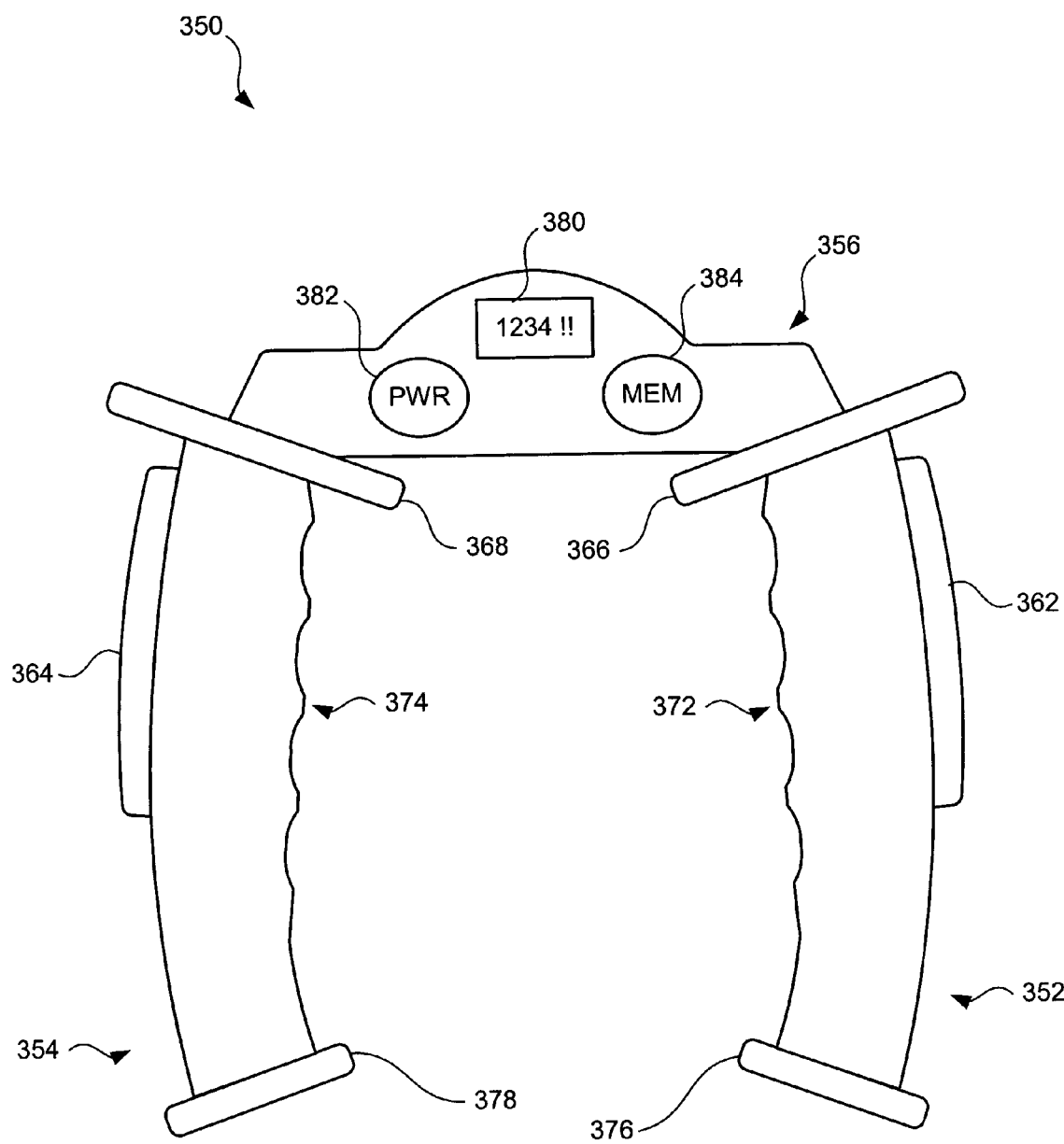
FIG. 9 is a plan view of a bilateral hand strength measurement device.

With reference to FIG. 9, a plan view of a bilateral hand strength measurement device 350 is shown. Bilateral hand device 350 includes a right side interface housing 352 and a left side interface housing 354 connected together by a center housing 356. Center housing 356 contains the electronics (not shown) discussed with reference to FIGS. 3–5. Center housing 356 also contains a display 380 which may function as any of the displays, indicators, or output devices described previously. In this exemplary embodiment, the display 380 shows a strength value ("1234") together with an alert signal ("!!"). Center housing 356 may further contain a power button 382 to turn the electronics on or off and a memory button 384 to scroll through measured strength values and threshold values stored in memory.

The right and left side interface housings 352/354 are ergonomically curved to be readily grasped by the user's hands, with the palms engaging large buttons 362/364, and the fingers engaging contoured grip surfaces 372/374, respectively. Upper flanges 366/368 and lower flanges 376/378 are disposed on opposite ends of the right and left interface housings 352/354, respectively, to serve as guides to position the user's hands thereon. Large buttons 362/364 are movably disposed in the right and left housings 352/354, and may actuate strength gauges (not visible) in a manner as discussed with reference to FIGS. 7 and 8. The strength gauge (not visible) may comprise, for example, two discrete gauges contained in right side interface housing 352 and left side interface housing 354, respectively, or a differential gauge contained in center housing 356. The large buttons 362/364 and the surfaces 372/374 collectively define the right and left interfaces, respectively, which are configured to provide independent force inputs (as opposed to force inputs acting in opposition of each other).

With reference to FIG. 10 a plan view of a bilateral pneumatic hand strength measurement device 400 is shown. Bilateral pneumatic hand device 400 includes a right side interface bulb 402 and a left side interface bulb 404 connected together by a center housing 406. Center housing 406 contains the electronics (not shown) discussed with reference to FIGS. 3–5. Center housing 406 also contains a display 420 which may function as any of the displays, indicators, or output devices described previously. In this exemplary embodiment, the display 420 shows a strength value ("1234") together with an alert signal ("!!"). Center housing 406 may further contain a power button 422 to turn the electronics on or off and a memory button 424 to scroll through measured strength values and threshold values stored in memory.

The right and left side interface bulbs 402/404 are ergonomically shaped to be readily grasped by the user's hands, with the thumbs positioned in recesses 416/418, and the fingers engaging contoured grip surfaces 412/414, respectively. The right and left side interface bulbs 402/404 are configured to provide independent force inputs (as opposed to force inputs acting in opposition of each other) and may comprise closed hollow compressible volumes in fluid communication with a strength gauge (e.g., discrete pressure gauges or a single differential pressure gauge) contained in center housing 406 via tubes 410/408. Tube 410 may comprise, for example, a rigid tube structure to control the position of the housing 406 with respect to the left interface 404, and tube 408 may comprise, for example, a flexible tube to permit relatively free movement and positioning of the right side interface 402 with respect to the left side interface 404.

Figure 11:
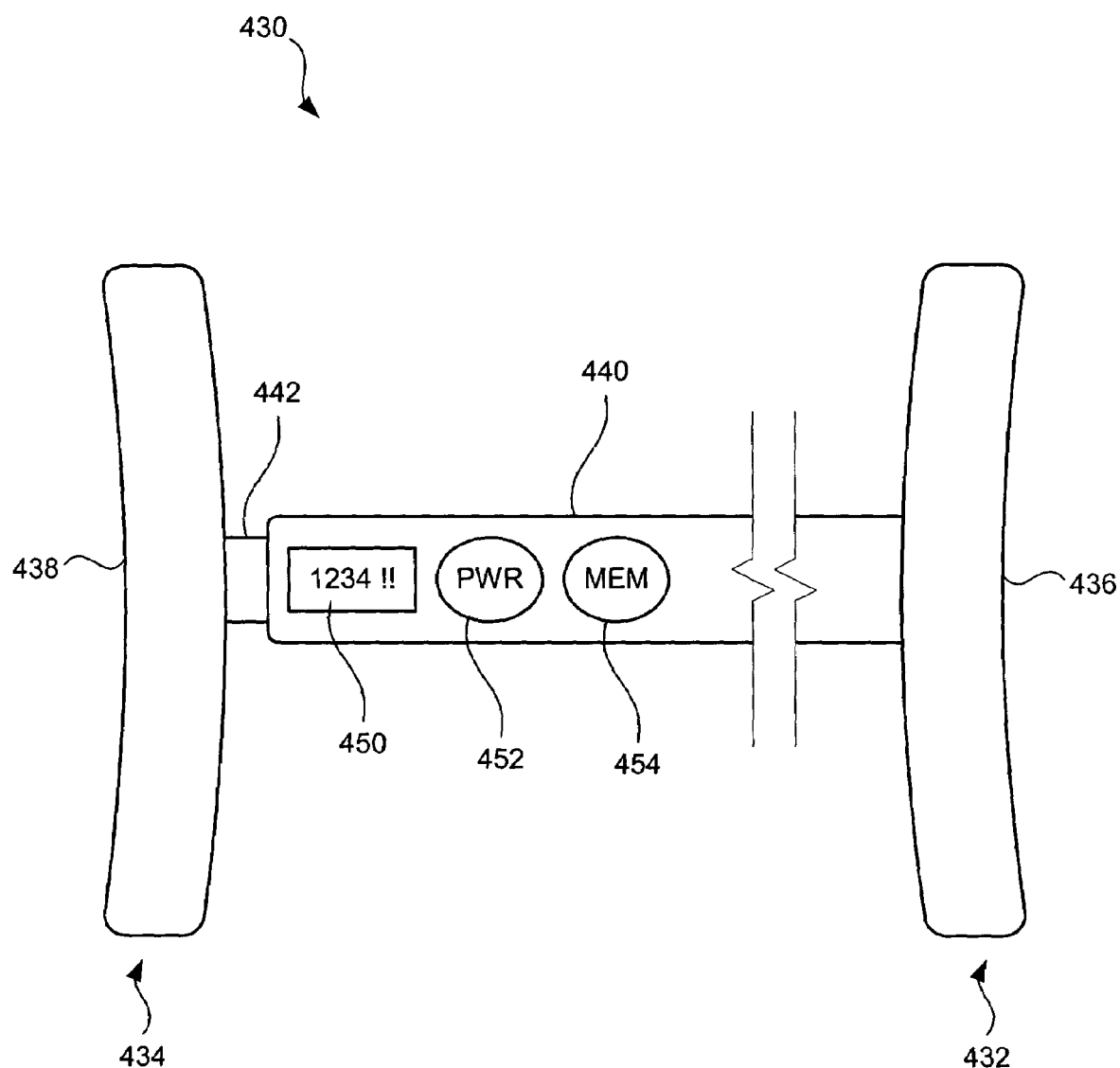
FIG. 11 is a plan view of a bilateral arm and leg strength measurement device.

With reference to FIG. 11, a plan view of a bilateral arm and leg strength measurement device 430 is shown. Bilateral arm/leg device 430 includes a right side interface 432 and a left side interface 434 connected together by a chamber 440 and piston 442 assembly, respectively. The piston 442 assembly is movably disposed in the chamber housing 440 to actuate a differential strength gauge (not visible) disposed in the chamber housing 440. Chamber housing 440 contains the electronics (not shown) discussed with reference to FIGS. 3–5, in addition to a display 450 which may function as any of the displays, indicators, or output devices described previously. In this exemplary embodiment, the display 450 shows a strength value ("1234") together with an alert signal ("!!"). Chamber housing 440 may further contain a power button 452 to turn the electronics on or off and a memory button 454 to scroll through measured strength values and threshold values stored in memory. The right and left side interfaces 432/434 are ergonomically curved to define concave contours 436/438 that readily engage the right and left inside forearms or right and left inside thighs of the user, respectively. The right and left side interfaces 432/434 are configured to provide to force inputs acting in opposition of each other (as opposed to independent force inputs).

Figure 12:
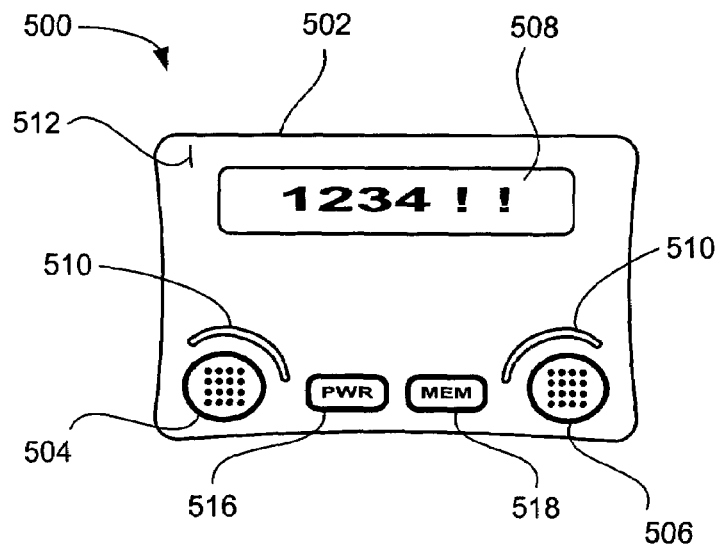
FIGS. 12A–12C are top, bottom, and side views, respectively of an alternative bilateral finger strength measurement device.
Figure 12:
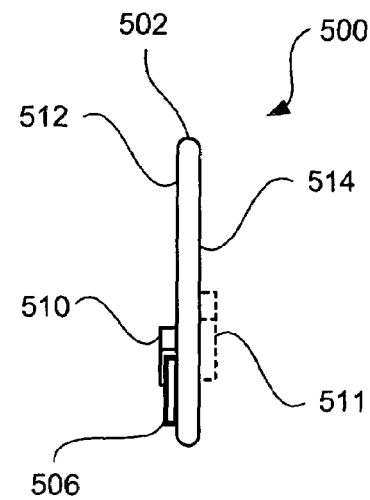
Figure 12:
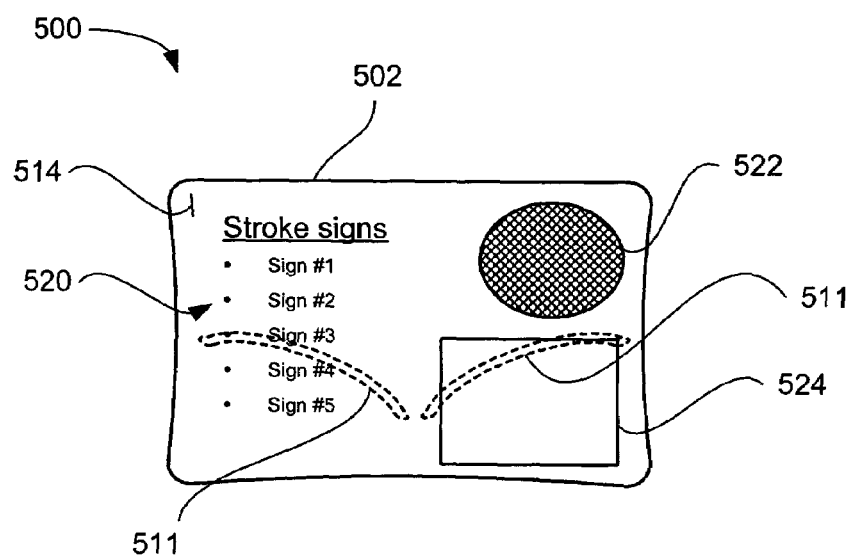

With reference to FIGS. 12A–12C, top, side and bottom views, respectively, of a bilateral finger strength measurement device 500 are shown. Bilateral finger device 500 is sized to be readily portable and carried in the user's clothing, pockets, wallet or purse, much like a credit card, or attached to a commonly carried item such as a key chain. For purposes of illustration, the size of the device 500 may be approximated as a credit card or parking card, while possibly thicker to accommodate the electronics and other workings therein.

Bilateral finger device 500 includes a housing 502 which contains the strength gauge and electronics (not shown) discussed with reference to FIGS. 3–5. Housing 502 also contains a display 508 which may function as any of the displays, indicators, or output devices described previously. In this exemplary embodiment, the display shows a strength value ("1234") together with an alert signal ("!!"). The strength gauge (not visible) contained in housing 502 may comprise, for example, two discrete gauges as discussed with reference to FIG. 7 or a differential gauge as discussed with reference to FIG. 8.

Housing 502 further contains a pair of buttons 504/506 movably disposed therein which protrude from the top surface 512 of the housing. The buttons 504/506 and the bottom surface 514 of the housing collectively define the right and left interfaces, which are configured to provide independent force inputs (as opposed to force inputs acting in opposition of each other). The buttons 504/506 and the bottom surface 514 of the housing are configured to be grasped or pinched between the user's right and left thumbs and the user's right and left (index) fingers, respectively. Housing 502 may further contain a power button 516 to turn the electronics on or off and a memory button 518 to scroll through measured strength values and threshold values stored in memory.

The buttons 504/506 and the bottom surface of the housing 502 may include surface irregularities (e.g., texture, protrusions, etc.) to give the user tactile feedback indicating when the interfaces are properly engaged. In addition, top stop members 510 may be placed adjacent the buttons 504/506 on top side 512 to engage the tips of the user's thumbs, and bottom stop members 511 may be provided on the bottom side 514 (shown in phantom) to engage the index fingers of the user. For example, the top and bottom stop members 510/511 may comprise raised ridges extending from the surface of the housing 502. The top and bottom stop members 510/511 further ensure that the thumbs are consistently positioned and that the interfaces are properly engaged.

Figure 13A:
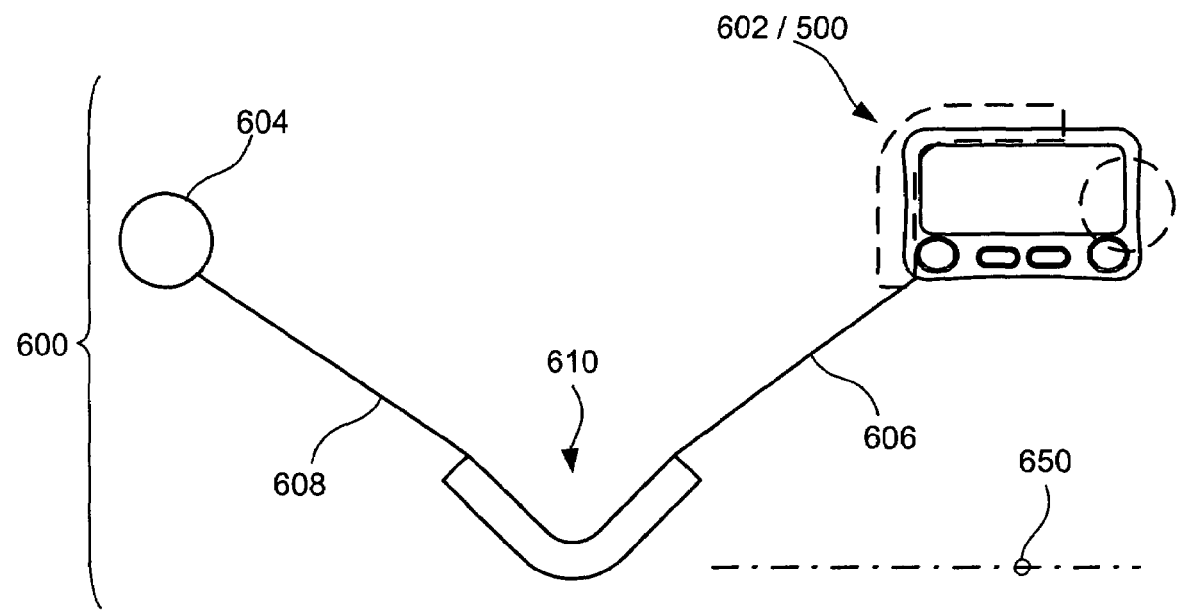
FIGS. 13A and 13B are schematic plan views of an arm drift measurement device.
Figure 13B:
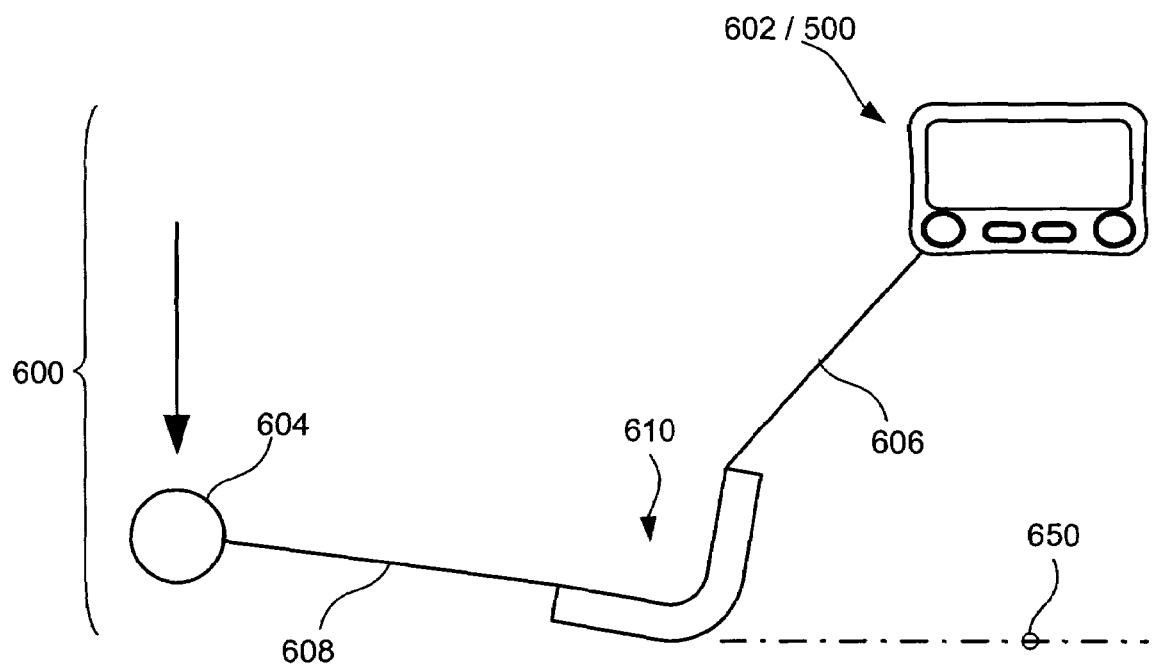

With reference to FIGS. 13A and 13B, plan views of an arm drift measurement device 600 are shown. Arm drift measurement device 600 is similar to the strength measurement devices described previously, with the general exception that device 600 compares the ability of the right and left sides of the user to maintain the same position and/or force application. In this exemplary embodiment, arm drift measurement device 600 compares the ability of the user to maintain both arms in a symmetrical extended level (horizontal) position over a period of time. Those skilled in the art will recognize that the device 600 may be used for other anatomical and positional comparisons, such as measuring finger, hand, arm, or leg drift in horizontal, vertical or other positions.

In such embodiments, the degree of displacement (i.e., drift) and/or the amount of displacement over time (i.e., drift rate) of the right and left sides may be compared. Drift or drift rate above a predetermined threshold value may be indicative of hemiparesis. Accordingly, the arm drift measurement device 600 provides an alternative to the strength measurement devices described previously, but may be used in a similar manner. To this end, the same or similar signal processing electronics, computing hardware and software, and algorithms as described previously may be implemented with arm drift measurement device 600.

The arm drift measurement device 600 may be integrated into measurement device 500 as shown, or may comprise a stand-alone device. As shown in phantom in FIG. 13A, the components of the arm drift measurement device 600 may be retracted into and stored in measurement device 500.

The arm drift measurement device 600 includes an inclinometer 610 coupled to right grip 602 and left grip 604 by elongate members 606 and 608, respectively. The grips 602 and 604 may be ergonomically configured to be grasped by the user's hand and/or fingers. In the illustrated embodiment, the right hand grip 602 comprises device 500 and the left hand grip 604 comprises a finger ring.

The elongate members 606 and 608 are substantially equal in length and may be flexible or rigid. The right elongate member 606 may accommodate electrical leads to provide electrical communication between the inclinometer 610 and the electronics carried by device 500. The end portions of the elongate members 606 and 608 and/or the connections at the ends of the elongate members 606 and 608 may be configured to have negligible torque transmission thus transmitting only linear forces along their length and permitting the inclinometer 610 to hang freely.

In use, the arm drift measurement device 600 is protracted from its stored configuration, which may automatically turn on or otherwise activate the device 600. With the right and left hands, the user holds the right grip 602 and the left grip 604, respectively, such that the grips are substantially horizontally level (i.e., level with horizontal line 650) as shown in FIG. 13A. In this position, the inclinometer 610, which is also horizontally level, may detect its level position and initiate a measurement sequence. Failure to establish a level horizontal position within a specified period of time may be indicative of hemiparesis and therefore trigger an alarm.

Once a horizontal position is established, a timer carried by the electronics in device 500 may be started, and an indicator such as an audible signal may be trigger to notify the user to try to maintain the horizontal position. If the user is unable to maintain level arms as shown in FIG. 13B, the inclinometer 610 measures the degree of drift, and the timer permits calculation of drift rate. After a predefined test period has elapsed (e.g., 5 to 30 seconds), another indicator is triggered to notify the user that the test is complete. If the drift or drift rate during the test period exceeds a predetermined threshold value, hemiparesis is detected and further action may be taken in accordance with prior embodiments.

If the drift or drift rate during the test period does not exceed the predetermined threshold value, hemiparesis is not detected.

The inclinometer 610 may comprise any of a variety of miniature inclinometers known to those skilled in the art. The inclinometer 610 may function in a binary mode (i.e., activated or deactivated within a specified incline range; e.g., a mercury switch), a graduated/digital mode (i.e., degree of incline detected in increments) or a continuous/analog mode (i.e., degree of incline detected in continuum). By way of example, not limitation, an inclinometer 610 operating in a binary mode is schematically illustrated in FIGS. 14A and 14B.

Figure 14A:
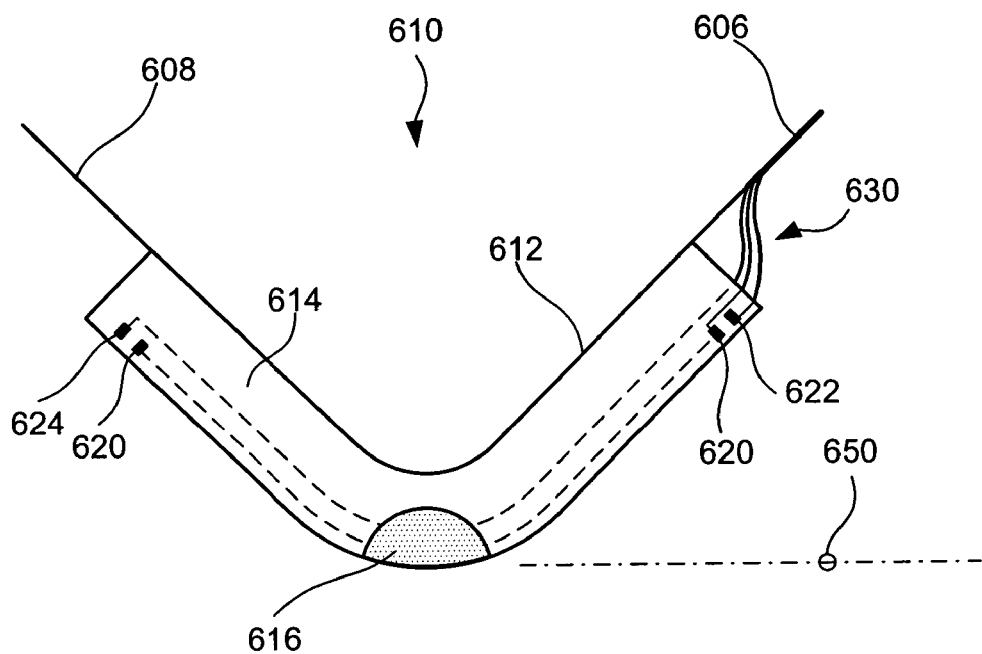
FIGS. 14A and 14B are schematic views of an example of an inclinometer for use in the arm drift measurement device shown in FIGS. 13A and 13B.
Figure 14B:
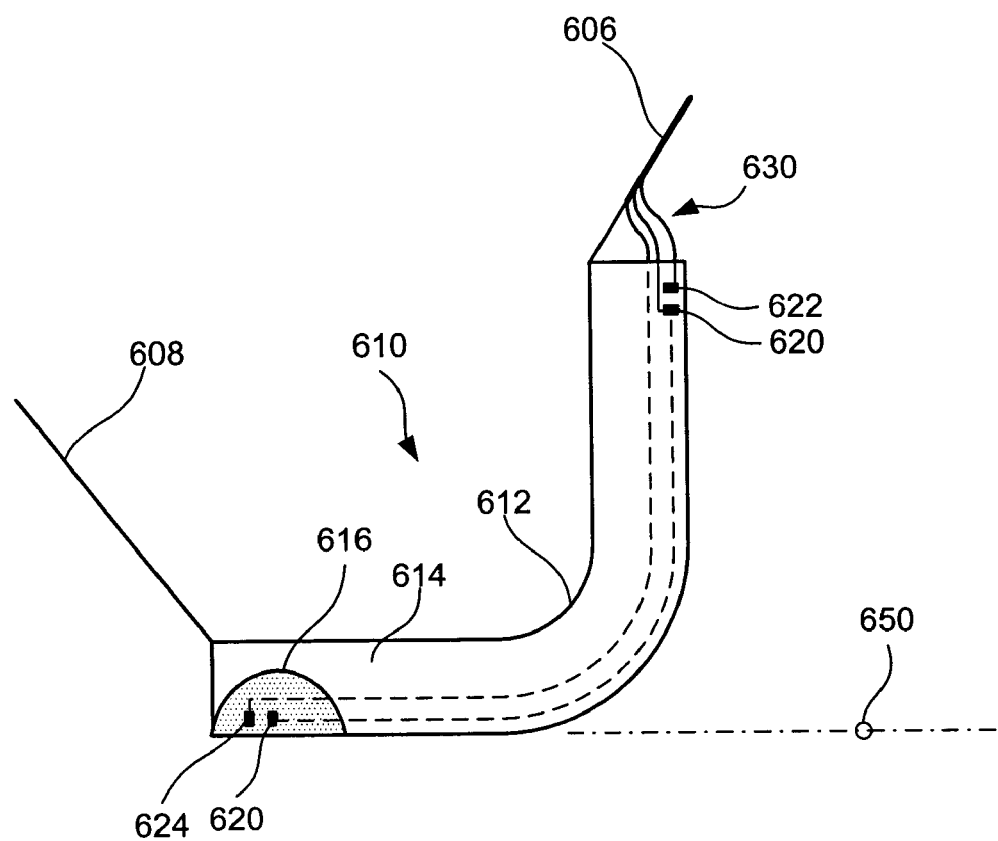

In the embodiment illustrated in FIGS. 14A and 14B, the inclinometer 610 includes a sealed tubular vessel 612 containing a relatively non-conductive gas fill 614 and a relatively conductive liquid droplet 616 (e.g., mercury), which may have a high degree of surface tension to maintain a unitary state. The tubular vessel 612 may be curved upward or downward to decrease or increase sensitivity, respectively, to changes in incline. For example, to detect gross deviations in drift, the vessel 612 may be curved upward as shown. The angle of curvature relative to horizontal level 650 may correspond to the threshold inclination value. As an alternative, the gas fill 614 and liquid droplet 616 may be interchanged with a non-conductive gas bubble 616 and a conductive liquid fill. In this alternative embodiment, the opposite effect of curvature may be expected.

The inclinometer 610 further includes conductive pads 620, 622 and 624 exposed to the inside of the vessel 612, with the common pad 620 disposed at the right and left ends of the vessel 612, the right pad 622 disposed at the right end of the vessel 612, and the left pad 624 disposed at the left end of the vessel 612. The pads 620, 622 and 624 are connected to leads 630 which travel along elongate member 606 to the electronics contained in device 500. When the vessel 612 is inclined a sufficient amount as dictated by the curvature of the vessel, the conductive liquid flows in the downward direction and establishes an electrical connection (closed circuit) between the common pad 620 and either the right pad 622 or he left pad 624, depending on the direction of incline. Absent sufficient incline, no electrical connection is established (open circuit) between the pads 620, 622 and 624. With this arrangement, inclination at or beyond a threshold degree to the right or left may be detected.

Figure 15A:
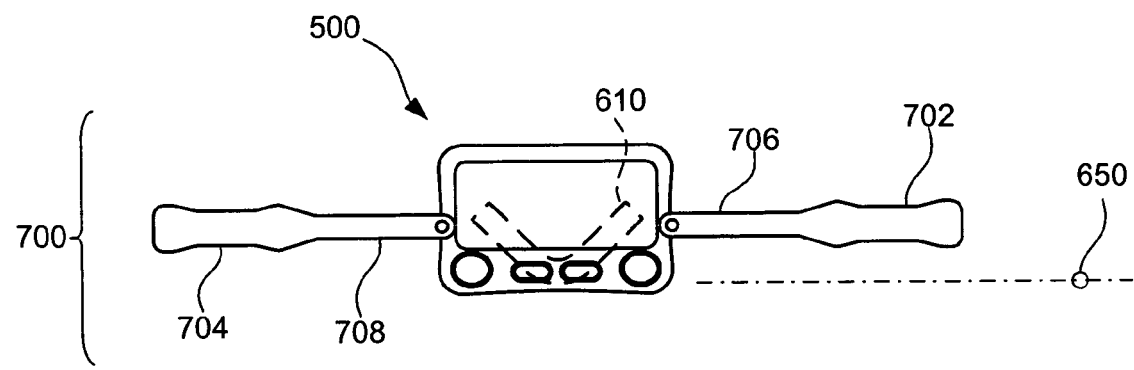
FIGS. 15A and 15B are schematic plan views of an alternative arm drift measurement device.
Figure 15B:
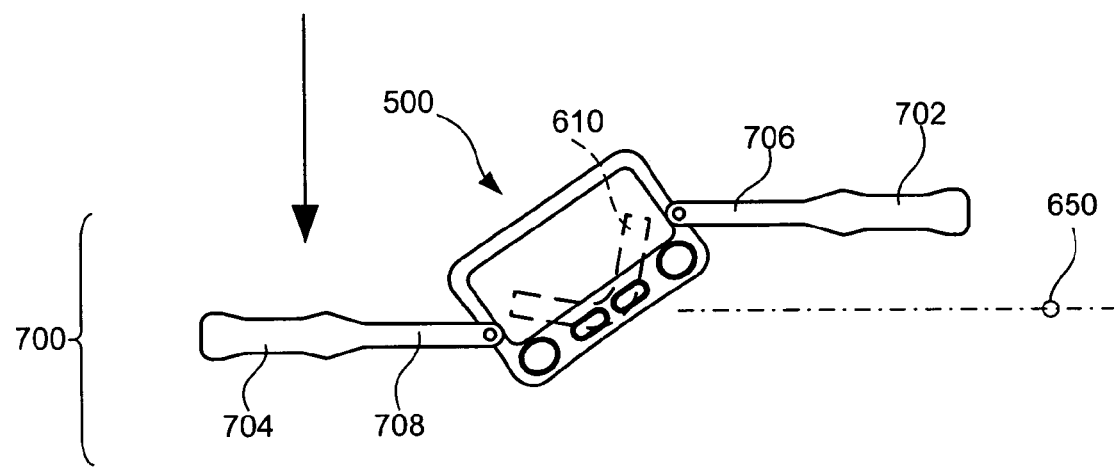

With reference to FIGS. 15A and 15B, an alternative arm drift measurement device 700 is shown. Arm drift measurement device 700 is similar to arm drift measurement device 600, with the general exception that the inclinometer 610 (shown in phantom) is incorporated into device 500. A pair of right and left grips 702 and 704, respectively, are connected to the device 500 by relatively rigid elongate members 706 and 708, respectively. The elongate members 706 and 708 have substantially the same length and are pivotally connected to the device 500. Both the grips 702 and 704 and the elongate members 706 and 708 may be retractably stored in the device 500. The operation and function of arm drift measurement device 700 is otherwise substantially the same as arm drift measurement device 600.

As an alternative to the single inclinometer 610 utilized by the arm drift measurement devices 600 and 700 described above, two or more inclinometers 610 may be used. In this alternative embodiment, a first inclinometer may be secured to the user's right side (e.g., hand, forearm, or upper arm), and a second inclinometer may be secured to the user's left side in a symmetrical position (i.e., the same anatomical position: e.g., hand, forearm, or upper arm). The relative inclination of the right and left sides may then be compared in a similar manner as with the bilateral strength measurement devices described previously.

Ataxia Detection Devices & Methods

The measurement devices described above (e.g., device 500) may be used in addition or in the alternative to detect ataxia by measuring dexterity. In this alternative embodiment, the strength measurement gauges may be replaced with switches (e.g., normally open momentary contact switches), contact sensors, or other components that may be readily activated and deactivated. In addition, the switches may incorporate the ability to illuminate.

To measure dexterity, the switches (left right or both) may be activated (e.g., opened or closed) and the number of times the switches are activated within a given time frame, or the elapsed time taken to activate the switches a known number of times, or the frequency of actuation, may be measured. For example, the user may be prompted to actuate one side as many times as possible in a predetermined time frame, and subsequently or simultaneous actuate the other side as many times as possible in the same time frame. The user may be prompted by written instructions on the display, or by illuminating the switches in the desired sequence. The number of actuations or the frequency thereof (number divided by time frame) may be compared. For example, the left and right sides may be compared, the current measurements may be compared to historical data (e.g., left current to left historical and right current to right historical), and/or the current measurements may be compared to threshold values (e.g., left current to left threshold and right current to right threshold). Based on the comparison, a difference in the number or actuations or frequency thereof may be an indication of a loss in dexterity of the left or right side, which may be indicative of hemiparesis and stroke.

Aphasia Detection Devices & Methods

Figure 16:
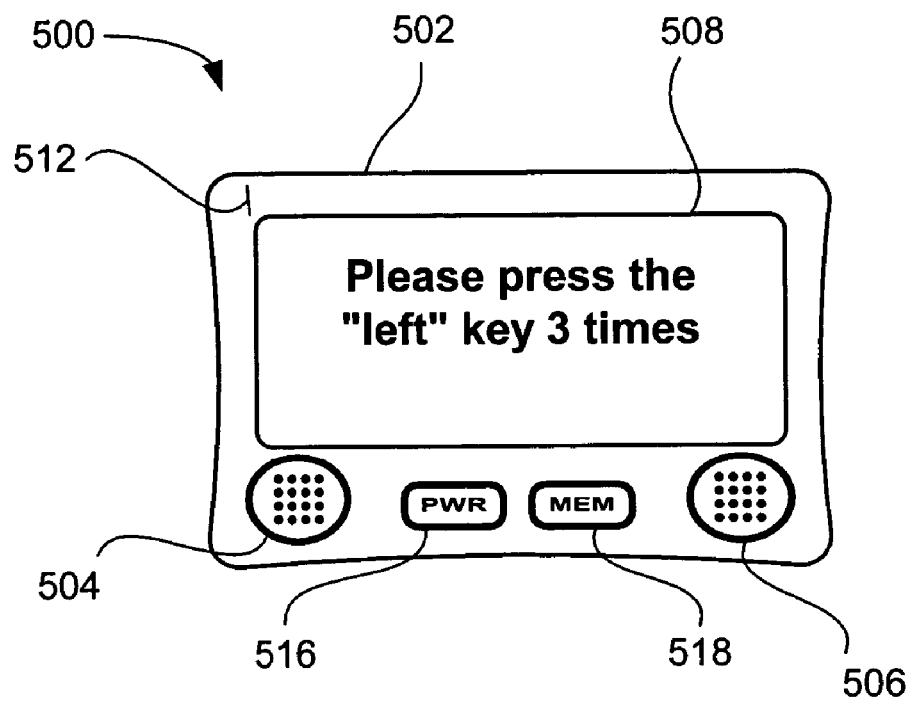
FIGS. 16 and 17 are schematic plan views aphasia detection devices.

With the same device (e.g., device 500) described above, receptive aphasia may be detected. To measure receptive aphasia, the user may be prompted to actuate one or both sides, and the user's response time and/or response correctness may be measured. The user may be prompted by written instructions on the display, or by illuminating the switches in the desired sequence. For example, the user may be prompted to press the right or left button a specific number of times as shown in FIG. 16, and the delay time and/or correctness of the response may be measured. Alternatively, the user may be prompted to actuate one or both sides in a specified sequence or pattern (e.g., right-left-right-both-right-left) and the delay time from prompt to correct actuation may be measured for each prompt. Optionally, the delay time may be weighted as a function of whether the correct switch is actuated. An incorrect response or a significant delay in response time may be indicative of receptive aphasia, and therefore stroke.

Figure 17:
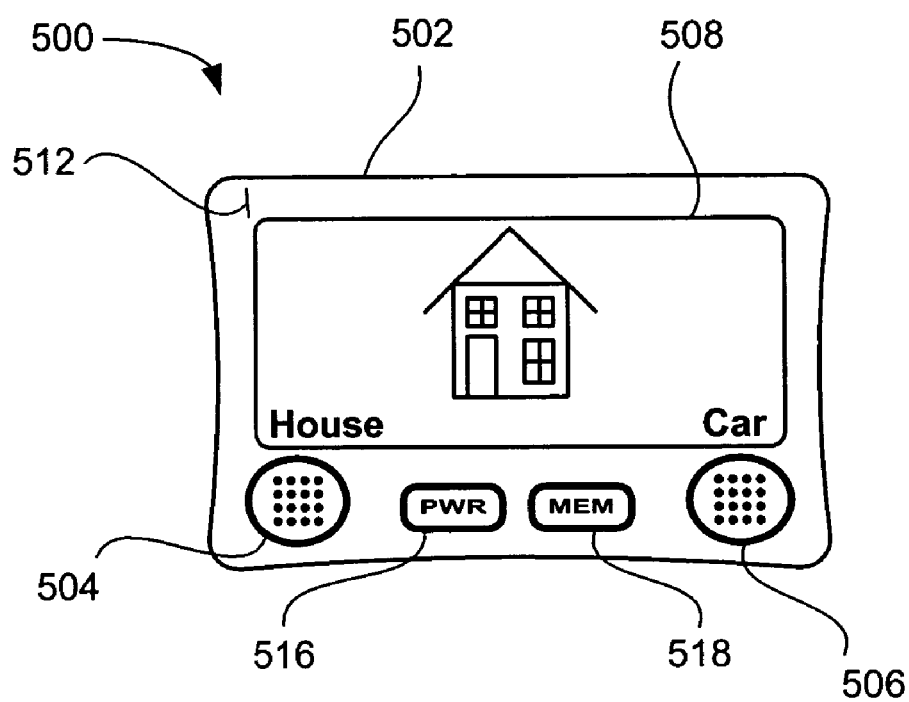

With a similar device (e.g., device 500) as described above, expressive aphasia may be detected. To measure expressive aphasia, the user may be posited with an image of an object and prompted to name the object by a multiple choice selection or by an audible response which may be recorded and evaluated by the device using voice pattern recognition techniques or subsequently evaluated by a physician, for example. An illustrative example is shown in FIG. 17, wherein the display posits an image of a house, and the user is prompted to name the object as either a house or a car. Optionally, the response may optionally be weighted as a function of response time. An incorrect response or a significant delay in response time may be indicative of expressive aphasia, and therefore stroke.

Dysarthria Detection Devices & Methods

With a similar device as described above (e.g., device 500), dysarthria may be detected. In this embodiment, the device may be modified to incorporate a microphone and recordation circuitry, and optionally incorporate voice pattern comparison capabilities. To measure dysarthria, the user may be prompted to say a word or phrase. The user may be prompted by displaying the text of the word or phrase or by audibly presenting a pre-recordation of the word or phrase, for example. The device then records the user's audible response. The recorded response may be compared to a previous recordation (e.g., by the user) of the same word or phrase utilizing voice pattern recognition techniques. Alternatively, the recorded response may be subsequently evaluated by medical personnel.

Other Warning Signs

In all embodiments of the measurement device, indicia of other warning signs of stroke may be provided to the user. The warning signs may be presented visually, audibly or by other means to alert the user of other signs of stroke which, when taken together with the measurement, may provide additional evidence or a higher confidence level of a stroke/non-stroke diagnosis. The most common warning signs of stroke according to the National Stroke Association and the American Heart Association are:

Sudden numbness or weakness of the face, arm or leg, especially on one side of the body;

Sudden confusion, trouble speaking or understanding;

Sudden trouble seeing in one or both eyes;

Sudden trouble walking, dizziness, loss of balance or coordination; and

Sudden, severe headache with no known cause.

With reference to FIG. 12C, the indicia may be provided to the user, for example, by including printed matter 520 on the measurement device (e.g., back side), by utilizing a speaker 522 or other audible transducer to audibly generate (e.g., speak) the warning signs, or by utilizing a visual display 524 such as an LCD to visually generate the warning signs. The indicia may be provided at all times as with the printed matter 520, or the indicia may be generated at select times such as when the device is powered on or when a measurement has been taken.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A device for detecting a symptom of stroke of a user, comprising: a user interface for obtaining a user measured response; an indicator; a processor connected to the user interface and the indicator; and a memory storage device connected to the processor, the memory storage device containing an algorithm executable by the processor, the algorithm defining a preset condition pertaining to the stroke symptom, and the algorithm activating the indicator if the measured response meets the preset condition, wherein the indicator urges the user to seek medical attention.

2. A device as in claim 1, wherein the preset condition corresponds to a condition of hemiparesis.

3. A device as in claim 1, wherein the preset condition corresponds to a condition of aphasia.

4. A device as in claim 1, wherein the preset condition corresponds to a condition of aphasia.

5. A device as in claim 1, wherein the preset condition corresponds to a condition of dysarthria.

6. A device as in claim 1, wherein the user interface comprises a right side interface configured to interface with a right side of the user and a left side interface configured to interface with a left side of the user, wherein the left side interface is configured to act independently of the right side interface.

7. A device as in claim 6, wherein the preset condition corresponds to a condition of hemiparesis.

8. A device as in claim 6, wherein the preset condition corresponds to a condition of ataxia.

9. A method of detecting a symptom of stroke of a user, comprising: providing a detection device including a user interface and an indicator; receiving a user response via the interface; measuring the user response; and activating the indicator if the user measured response meets a preset condition indicative of the stroke symptom, wherein the indicator urges the user to seek medical attention.

10. A method as in claim 9 wherein the stroke symptom comprises hemiparesis.

11. A method as in claim 10, wherein the step of receiving a user response comprises receiving a user response from the user's upper extremity.

12. A method as in claim 11, wherein the step of receiving a user response comprises receiving a user response from the user's arm.

13. A method as in claim 11, wherein the step of receiving a user response comprises receiving a user response from the user's hand.

14. A method as in claim 9, wherein the stroke symptom comprises ataxia.

15. A method as in claim 9, wherein the stroke symptom comprises aphasia.

16. A method as in claim, 9 wherein the stroke symptom comprises dysarthria.

17. A method of detecting a symptom of stroke of a user, comprising: providing a detection device including a right side user interface, a left side user interface, and an indicator; receiving a right side user response via the right side interface; receiving a left side user response via the left side interface; comparing the right side user measured response to the left side user measured response; and activating the indicator if the comparison meets a preset condition indicative of the stroke symptom, wherein the indicator urges the user to seek medical attention.

18. A method as in claim 17, wherein the preset condition corresponds to a condition of hemiparesis.

19. A method as in claim 17, wherein the preset condition corresponds to a condition of ataxia.

* * * * *